United States Patent [19]

Hagedorn et al.

[11] B 3,993,586
[45] Nov. 23, 1976

[54] WATER-SOLUBLE COMPLEX OF CUPROUS CHLORIDE, HYDROCHLORIC ACID AND AT LEAST ONE AMINE OR AMINE SALT

[75] Inventors: Ferdinand Hagedorn; Karlfried Wedemeyer; Rodulf Mayer-Mader, all of Cologne, Germany

[73] Assignee: Bayer Aktiengesellschaft, Germany

[22] Filed: Apr. 4, 1974

[21] Appl. No.: 457,850

[44] Published under the second Trial Voluntary Protest Program on February 10, 1976 as document No. B 457,850.

[30] Foreign Application Priority Data

Apr. 11, 1973 Germany............................ 2318115

[52] U.S. Cl. .......................... 252/429 R; 260/654 R
[51] Int. Cl.² ......................................... B01J 31/30
[58] Field of Search ............. 252/429 R; 260/654 R

[56] References Cited
UNITED STATES PATENTS

| | | | |
|---|---|---|---|
| 2,328,275 | 8/1943 | Heard ............................. | 260/663 |
| 2,503,264 | 4/1950 | Hampton ..................... | 252/429 R X |
| 3,078,283 | 2/1963 | Hay............................. | 252/429 R X |
| 3,388,176 | 6/1968 | Sheard ........................ | 252/429 R X |
| 3,651,019 | 3/1972 | Asscher et al. .................... | 260/77.2 |
| 3,819,730 | 6/1974 | Nakata et al................ | 252/429 R X |

*Primary Examiner*—Patrick P. Garvin
*Attorney, Agent, or Firm*—Connolly and Hutz

[57] ABSTRACT

Catalysts for the addition of hydrogen chloride to chloroprene for the preparation of 1,3-dichlorobutene-(2) in the liquid phase, constituting a complex of copper(I)chloride, aqueous hydrochloric acid, hydrogen chloride and a. a pyridine substituted with 1 to 3 alkyl groups on carbon atoms, which alkyl groups contain 1 or 2 carbon atoms, or b. an N,N-dialkyl substituted aniline, the N-substituted alkyl groups being straight chain groups containing 1 to 3 carbon atoms and the aromatic nucleus being optionally substituted with 1 or 2 methyl groups, the C/N atomic ratio in the molecule of the substituted aniline being <14, or c) diethylamine or d) triethylamine or e) the hydrochlorides of the above mentioned nitrogen compounds.

6 Claims, No Drawings

WATER-SOLUBLE COMPLEX OF CUPROUS CHLORIDE, HYDROCHLORIC ACID AND AT LEAST ONE AMINE OR AMINE SALT

This invention relates to catalysts for the preparation of 1,3-dichlorobutene-(2) in the liquid phase.

The synthesis of 1,3-dichlorobutene-(2) by the addition of hydrogen chloride to chloroprene has already been described. According to U.S. Pat. 2,102,611, hydrogen chloride can be added to chloroprene in the presence of a copper(I) halide/hydrochloric acid catalyst. Investigations carried out by Hatch et al, *J. Am. Chem. Soc.* 71, 1039 (1949) showed that 1,3-dichlorobutene-(2) is obtained from hydrogen chloride and chloroprene in a moderate yield (58%) when a complex catalyst prepared from copper(I) chloride, aqueous hydrochloric acid and ammonium chloride is used.

German Pat. No. 1,193,936 describes the addition of hydrogen chloride to chloroprene in the presence of non-ionic emulsifying agents and ammonium chloride (75 %).

The use of ultrasonic vibrations for the said reaction is also known (Japanese Pat. No. 158,294; 16.8.1943).

Lastly, German Offenlegungsschrift No. 2,060,378 describes copper(I) complex salt solutions by means of which selective addition of hydrogen chloride to vinyl acetylene can be achieved but in which subsequent reaction of the resulting chloroprene to form 1,3-dichlorobutene-(2) is substantially prevented.

With the catalysts known to the art conversion of the chloroprene into 1,3-dichlorobutene-(2) is not complete enough to avoid distillation of unreacted chloroprene, or its removal by some other method when isolating the desired product. As is well known, distillation of chloroprene is undesirable owing to the risk of polymerisation.

The highest conversions of chloroprene to 1,3-dichlorobutene-(2) presently known are not more than 90 %.

Another disadvantage of the catalysts already described for the preparation of 1,3-dichlorobutene-(2) is that they do not raise sufficiently the velocity of the aforesaid reaction and in some cases even decrease the reaction velocity (see below).

It has now been found that liquid copper(I) complex salt solutions prepared from copper(I) chloride, hydrochloric acid and a. a pyridine substituted with one or more alkyl groups, or
b. an N,N-dialkylsubstituted aniline or
c. diethylamine or
d. triethylamine or
e. the hydrochloride of the aforesaid nitrogen compounds 1. effect almost complete conversion of chloroprene to 1,3-dichlorobutene-(2) and
2. distinctly increase the reaction velocity of the above mentioned reaction compared with the velocity achieved with the compounds previously known.

These catalysts can easily be separated from the organic phase and used again without first being processed. For instance, diethyl and triethyl ammonium dichlorocuprate(I) catalysts, have a lower density than 1,3-dichlorobutene-(2) and separate out as a supernatant layer after the reaction.

Another advantageous property of the catalysts according to the invention is that after separation of the layers they do not remain dissolved or emulsified in the dichlorobutene obtained by the reaction. However, the tendency of such liquids to emulsify or dissolve in 1,3-dichlorobutene-(2) increases with increasing chain length and number of alkyl groups in the N-substituents of copper(I) chloride-N-base complexes so that a catalyst prepared from N,N-di-n-butylaniline and copper(I) chloride/hydrochloric acid can not be separated so easily from 1,3-dichlorobutene.

The alkylsubstituted anilines and pyridines used for preparing the copper(I) complex in accordance with this invention are therefore restricted to those in which the atomic ratio of carbon to nitrogen in the molecule is less than 14.

Suitable alkyl substituted pyridines are pyridines which contain up to 3 C-alkyl substituents and in which these alkyl groups contain 1 or 2 carbon atoms. The following are given as examples: $\alpha$-, $\beta$- and $\gamma$-picoline; 2,6-dimethyl pyridine; 3,5-dimethylpyridine; 2,4,6-trimethylpyridine; 2-methyl-5-ethylpyridine; 3,5-diethylpyridine.

Suitable N,N-dialkyl substituted anilines are, for example, N,N-dimethyl-, N,N-diethyl- and N,N-di-n-propylaniline and N,N-dimethyl- and N,N-diethyl toluidine. Particularly suitable are N,N-dialkylsubstituted anilines in which the N-substituted alkyl groups are straight chain groups containing 1 to 3 carbon atoms and the aromatic nucleus is optionally substituted with 1 or 2 methyl groups and the C/N atomic ratio in the molecule is less than 14.

German Offenlegungsschrift No. 2,060,378 describes catalysts which when used for the hydrochlorination of vinyl acetylene to chloroprene prevent reaction of the resulting chloroprene to dichlorobutene. These catalysts include dichlorocuprate(I) complex compounds with hydrochlorides of methylamine, dimethylamine, ethanolamines or trimethylamine.

Complex compounds of this kind do in fact have a much weaker catalytic action in the hydrochlorination of chloroprene than the known copper(I) chloride/hydrochloric acid catalyst of the same copper concentration (see Table). These amine hydrochlorides complexed with copper(I) chloride/hydrochloric acid therefore have a marked retarding effect in the reaction of HCl with chloroprene. Furthermore, it was found that the ammonium/dichloro cuprate (I) complex $[NH_4]^+[CuCl_2]^-$ which has certain advantages over dichloro copper(I) acid ($HCuCl_2$) in the synthesis of chloroprene from vinyl acetylene has the most pronounced efficiency among the compounds investigated in reducing the reaction velocity of hydrogen chloride and chloroprene (see Table).

These findings and the comment in German Offenlegungsschrift No. 2,060,378 demonstrate that as regards the catalyst, the addition of hydrogen chloride to chloroprene cannot be compared with the addition of HCl to vinyl acetylene.

As the amine complexes mentioned in German Offenlegungsschrift No. 2,060,378 have a strong retarding effect on the addition of HCl to chloroprene, it is most surprising that the activity of copper(I) chloride/hydrochloric acid is so greatly increased by the inclusion of hydrochlorides of alkylpyridines, of N,N-dialkylated anilines, of diethylamine or of triethylamine in the complex compound that practically complete an selective conversion of chloroprene takes place within short reaction times.

The superiority of the catalysts according to the invention over those already known for the addition of hydrogen chloride to chloroprene shows particularly clearly when the reaction is carried out at atmospheric pressure.

The pyridinium-dichlorocuprate(I) complex which has already been mentioned for the addition of hydrogen chloride to vinyl acetylene also has a much weaker action than the catalysts claimed (see comparison example).

Another important feature is the high selectivity of chloroprene conversion to 1,3-dichlorobutene-(2) which can be achieved with the catalysts according to the invention. Subsequent reaction of 1,3-dichlorobutene-(2) with hydrogen chloride, which might be expected in view of the higher catalytic activity, does not take place under the reaction conditions employed here.

The catalysts may be prepared in known manner, for example by first dissolving the selected nitrogen compounds in aqueous hydrochloric acid and then preparing the complex by dissolving a quantity of copper(I) chloride which is approximately equimolar to the nitrogen compound and lastly saturating the clear solution with hydrogen chloride and stabilizing it with a small quantity of copper powder. The sequence in which the various components are dissolved is immaterial and has no effect on the catalyst activity.

The complex catalysts metnioned above are clear solutions except for the small quantity of copper powder suspended in them. If desired, the quantity of the aforesaid nitrogen compounds in them may be greater or smaller than corresponds to an equimolar proportion with respect to the copper(I) chloride. An excess of hydrochlorides, however, has no advantageous effect on the catalyst activity; similarly, if a less than equimolar quantity of hydrochlorides of bases are used (always based on the quantity of copper(I) compound), the catalytic activity is reduced.

From the working examples it can be seen that the concentration of the complex salt of copper(I) with the selected nitrogen bases in the solution may vary within wide limits.

From the experimental examples it can be seen that the concentration of copper(I) complex salt with the said nitrogen bases in the given solution may vary within wide limits.

The addition of hydrogen chloride to chloroprene with the aid of the catalysts according to the invention is generally carried out by mixing chloroprene with a catalyst solution which has been saturated with hydrogen chloride and stirring the mixture, introducing more HCl and removing the heat liberated in the reaction. If stirring is discontinued after the reaction, the catalyst phase separates from the dichlorobutene within a few seconds. Pure 1,3-dichlorobutene-(2) can easily be separated in this way while the catalyst solution is ready to be used again.

The catalysts may also advantageously be used in a continuous process. It is particularly in such a process that the high catalytic activity is an advantage when operating at ambient pressure (no HCl compression and no need for the release of pressure).

Although the catalysts according to the invention provide a sufficiently high reaction velocity in the HCl addition reaction at normal pressure, the velocity of addition can still be substantially improved by operating at elevated pressure. Provided the removal of heat produced in the reaction is controlled, previously unoptainable volume/time yields can then be achieved with the aid of the catalysts.

The temperature range of optimum activity is between about 10° and 50°C. At atmospheric pressure, reaction temperatures of about 10 to 40°C are preferred.

The catalyst solutions can be used again as often as required without any loss in activity being observed. Any organic impurities introduced are always dissolved out of the catalyst by means of the dichlorobutene formed in the reaction.

The following Examples serve to explain the preparation and action of the catalysts according to the invention.

EXAMPLE 1

242 Parts by weight of 2-methyl-5-ethylpyridine are added dropwise to 170 parts by volume of concentrated aqueous hydrochloric acid with stirring and cooling, 198 g of copper(I) chloride are dissolved in the hydrochloride solution and the catalyst is saturated with HCl gas.

250 Parts by volume of chloroprene are added to 500 parts by volume of this catalyst. The mixture is stirred without pressure at 25°C and treated with gaseous hydrogen chloride at the same time until the calculated quantity of hydrogen chloriide has been absorbed. The reaction is finished after 18 minutes. The chloroprene content in the organic phase is then only 0.4%, the remainder consisting of 1,3-dichlorobutene-(2).

If for comparison a pyridine-copper(I) complex catalyst of the same copper concentration and the same concentration of N-base hydrochloride is used under the same reaction conditons and with the same volumetric ratio of catalyst to chloroprene, then the chloroprene conversion after 18 minutes is only 69.3%.

EXAMPLE 2

The 2-methyl-5-ethyl-pyridine catalyst described in Example 1 is diluted with concentrated aqueous hydrochloric acid in a volumetric ratio of 1 : 1 and saturated with hydrogen chloride and used for chloroprene conversion as described in Example 1. The reaction time is now 45 minutes in order to obtain a chloroprene conversion of 99.2%.

EXAMPLE 3

A catalyst is prepared as described in Example 1 from 190 parts by volume of concentrated hydrochloric acid, 186 parts by weight of γ-picoline and 198 parts by weight of copper(I) chloride and saturated with hydrogen chloride and used for chloroprene conversion as described in Example 1. After 38 minutes, more than 99% of the chloroprene put into the reaction have been converted into 1,3-dichlorobutene-(2).

EXAMPLE 4

The catalyst described in Example 3 is diluted with concentrated hydrochloric acid at a volumetric ratio of 1 : 1 and saturated with hydrogen chloride. When chloroprene conversion is carried out as described in Example 1, 99.6% of the chloroprene put into the reaction has been converted into 1,3-dichlorobutene-(2) after 50 minutes.

EXAMPLE 5

When the catalyst from Example 4 is again diluated with concentrated hydrochloric acid using a ratio of 1 : 1 and the resulting complex solution is used as catalyst for converting chloroprene into dichlorobutene under the conditions indicated in Example 1, chloroprene conversion takes 80 minutes (98.8% dichlorbutene).

position of the organic phase is analysed gas-chromatographically. Stirring is discontinued when the calculated quantity by weight of hydrogen chloride has been absorbed. The phases then separate. The dichlorobutene content and residual chloroprene content in the organic phase are determined. The following Table shows the nitrogen bases used for the various catalyst solutions, the reaction time and the gas chromatographic analyses of the organic phase.

Table

Effect of N-compounds in the dichlorocuprate(I) complex on the velocity of addition of HCl

| | N-compound | Reaction time (minutes) | Dichlorobutene (%) | Residual chloroprene (%) |
|---|---|---|---|---|
| Comparison Examples | Ammonia | 205 | 93.2 | 6.7 |
| | Methylamine | 140 | 93.4 | 6.2 |
| | Ethylamine | >>120 | — | — |
| | Ethanolamine | >>120 | — | — |
| | Triethanolamine | >>120 | —. | — |
| | Copper(I) chloride/hydrochloric acid (without N-compound) | 90 | 96.2 | 3.8 |
| Example 7 | α-Picoline | 41 | 99.2 | 0.8 |
| Example 8 | γ-picoline | 40 | 99.4 | 0.6 |
| Example 9 | N,N-Dipropyl-aniline | 35 | 99.3 | 0.7 |
| Example 10 | Diethylamine | 35 | 99.3 | 0.7 |
| Example 11 | Triethylamine | 30 | 98.6 | 0.2 |
| Example 12 | 2,4,6-Trimethyl-pyridine | 29 | 99.5 | 0.4 |
| Example 13 | N,N-Dimethyl-aniline | 27 | 99.6 | 0.2 |
| Example 14 | N,N-Diethyl-aniline | 24 | 98.9 | 0.8 |
| Example 15 | 2-Methyl-5-ethyl-pyridine | 22 | 98.6 | 0.3 |

EXAMPLE 6

744 Parts by weight of γ-picoline are dissolved in 2880 parts by volume of concentrated hydrochloric acid at 25° to 30°C with stirring and cooling. 792 Parts by weight of copper(I) chloride are then added and the solution is saturated with gaseous hydrogen chloride at 25°C. The catalyst is freed from copper(II) compounds by the addition of 10 parts by weight of copper powder.

2000 Parts by volume of chloroprene which has been stabilized with 100 to 150 ppm of phenothiazine are added dropwise to 4000 parts by volume of this catalyst ($D = 1.32$) with stirring and cooling at such a rate that the reaction temperature is maintained at about 25°C while at the same time the reaction mixture is treated with gaseous hydrogen chloride without pressure (hydrogen chloride passed over the surface). The reaction finishes after 45 minutes. The chloroprene content then remaining in the mixture has dropped to below 1%. 2641 Parts by weight of 99.6% 1,3-dichlorobutene-(2) are separated from the catalyst phase. Yield 98% of the theory.

EXAMPLES 7 TO 15

Preparation of the catalyst solutions:

4.5 Parts by weight of copper(I) chloride and an equimolar quantity by weight of the given nitrogen base are dissolved in aqueous hydrochloric acid which is at the same time treated with gaseous hydrogen chloride, 50 parts by volume of a clear complex solution saturated with hydrogen chloride being finally obtained. This solution is stabilized with a pinch of copper powder.

176 Parts by weight of chloroprene which has been stabilized with 100 to 150 ppm of phenothiazine and 50 parts by volume of catalyst are treated with gaseous hydrogen chloride in an autoclave with stirring and cooling at 25°C and a pressure of 2 atmospheres gauge. The speed of stirring is kept constant. The weight of hydrogen chloride absorbed is controlled and the com- The catalysts obtained according to Examples 10 and 11 separate after chloroprene conversion as phases of lower specific gravity above the 1,3-dichlorobutene-(2) phase.

EXAMPLE 16

500 Parts by volume of a catalyst solution which contains 99 parts by weight of copper(I) chloride and an equimolar quantity by weight of 4-diethylaminotoluene and which is saturated with gaseous hydrogen chloride is prepared.

250 Parts by volume of chloroprene are reacted with hydrogen chloride in the presence of a catalyst in accordance with Example 1. The reaction time is 45 minutes. 99.4% of the chloroprene is converted into 1,3-dichlorobutene-(2).

EXAMPLE 17

A catalyst is prepared as described in Example 16 but using 2-dimethylaminotoluene instead of 4-diethylaminotoluene.

Chloroprene conversion is carried out as described in Example 1 in the presence of 500 parts by volume of catalyst solution. The reaction time is 45 minutes. 99.1% of the chloroprene is converted into 1,3-dichlorobutene-(2).

EXAMPLE 18

500 Parts by volume of a catalyst solution which contains 99 parts by weight of copper(I) chloride and an equimolar quantity by weight of 2,6-dimethylpyridine and which is saturated with hydrogen chloride are prepared.

250 Parts by volume of chloroprene are reacted with hydrogen chloride in the presence of catalyst as described in Example 1. The reaction time is 45 minutes. 99% of the chloroprene is converted in 1,3-dichlorobutene-(2).

We claim:

1. A composition consisting essentially of the aqueous phase reaction product of:
   I. cuprous chloride,
   II. hydrochloric acid and
   III. at least one amine or amine salt having an atomic ratio of carbon to nitrogen less than 14 and being either
      a. a pyridine having 1 to 3 alkyl groups as carbon atom substituents thereof,
      b. an N,N-dialkylaniline or said aniline having the aromatic nucleus thereof substituted with one or two methyl groups,
      c. diethylamine,
      d. triethylamine or
      e. a hydrochloride of one of the amines of a to d,
   reactants I–III for forming said composition being present in amounts producing a water-soluble complex useful as a catalyst for the addition of hydrogen chloride to chloroprene for preparing 1,3-dichlorobutene-(2) in the liquid phase.

2. The composition of claim 1 including copper powder as a stabilizer.

3. The composition of claim 1 in which each of the alkyl groups of III a have from 1 to 2 carbon atoms.

4. The composition of claim 1 wherein the alkyl groups on the nitrogen atom of III b are straight chain having from 1 tp 3 carbon atoms.

5. The composition of claim 1 in which the amine or amine salt of III is present in an amount substantially equimolar to the cuprous chloride of I.

6. The composition as claimed in claim 1 in which the hydrochloric acid of II is present in an amount which is at least equimolar to the cuprous chloride of I.

* * * * *